United States Patent [19]

Parodi

[11] Patent Number: 6,117,124
[45] Date of Patent: *Sep. 12, 2000

[54] DEVICE AND METHOD TO DO ARTERIOGRAPHIES AND ANGIOPLASTIES WITH A BALLOON AND WITHOUT INJECTING A CONTRASTING MEDIA IN THE VESSEL LUMEN

[76] Inventor: Juan Carlos Parodi, Don Bosco 3235, Lomas de San Isidro, 1642 - Province of Buenos Aires, Argentina

[ * ] Notice: This patent issued on a continued prosecution application filed under 37 CFR 1.53(d), and is subject to the twenty year patent term provisions of 35 U.S.C. 154(a)(2).

[21] Appl. No.: 08/751,909

[22] Filed: Nov. 18, 1996

[30] Foreign Application Priority Data

Jan. 26, 1996 [AR] Argentina .................................. 335193

[51] Int. Cl.⁷ .................................................. A61M 31/00
[52] U.S. Cl. ........................... 604/509; 604/96; 604/101; 604/194
[58] Field of Search ............................. 604/96–102, 500, 604/507–509; 606/192, 194

[56] References Cited

U.S. PATENT DOCUMENTS

| | | | |
|---|---|---|---|
| 4,301,803 | 11/1981 | Handa et al. | 604/96 |
| 4,909,258 | 3/1990 | Kuntz et al. | 128/658 |
| 4,911,163 | 3/1990 | Fina | 606/127 |
| 4,921,483 | 5/1990 | Wijay et al. | 604/96 |
| 5,002,532 | 3/1991 | Gaiser et al. | 604/101 |
| 5,092,846 | 3/1992 | Nishijima et al. | 604/165 |
| 5,171,299 | 12/1992 | Heitzmann et al. | 604/100 |
| 5,201,756 | 4/1993 | Horzewski et al. | 606/198 |
| 5,209,728 | 5/1993 | Kraus et al. | 604/96 |
| 5,324,263 | 6/1994 | Kraus et al. | 604/96 |
| 5,360,443 | 11/1994 | Barone et al. | . |
| 5,411,016 | 5/1995 | Kume et al. | 604/96 |
| 5,415,635 | 5/1995 | Bagaoisn et al. | 604/96 |
| 5,447,797 | 9/1995 | Sogard et al. | 604/101 |
| 5,514,092 | 5/1996 | Forman et al. | 604/101 |
| 5,522,880 | 6/1996 | Barone et al. | . |
| 5,536,252 | 7/1996 | Imran et al. | 604/101 |
| 5,674,198 | 10/1997 | Leone | 604/101 |
| 5,707,358 | 1/1998 | Wright | 604/96 |
| 5,728,068 | 3/1998 | Leone et al. | 604/101 |
| 5,820,585 | 10/1998 | Mobin-Uddin et al. | 604/53 |

*Primary Examiner*—Wynn Wood Coggins
*Assistant Examiner*—Deborah Blyveis
*Attorney, Agent, or Firm*—Tobor, Goldstein & Healey, L.L.P.

[57] ABSTRACT

A brand new device and a method to do arteriographies which allow simultaneous angioplasties by using a catheter and a balloon capable of copying the narrowed portion of the artery under study, providing the contrast required to view the artery via a contrasting medium which is circumscribed within the diagnosis balloon and which is not in relationship with the patient's tissue; therefor, the catheter has a diagnosis balloon which may be filled with the contrasting medium.

20 Claims, 3 Drawing Sheets

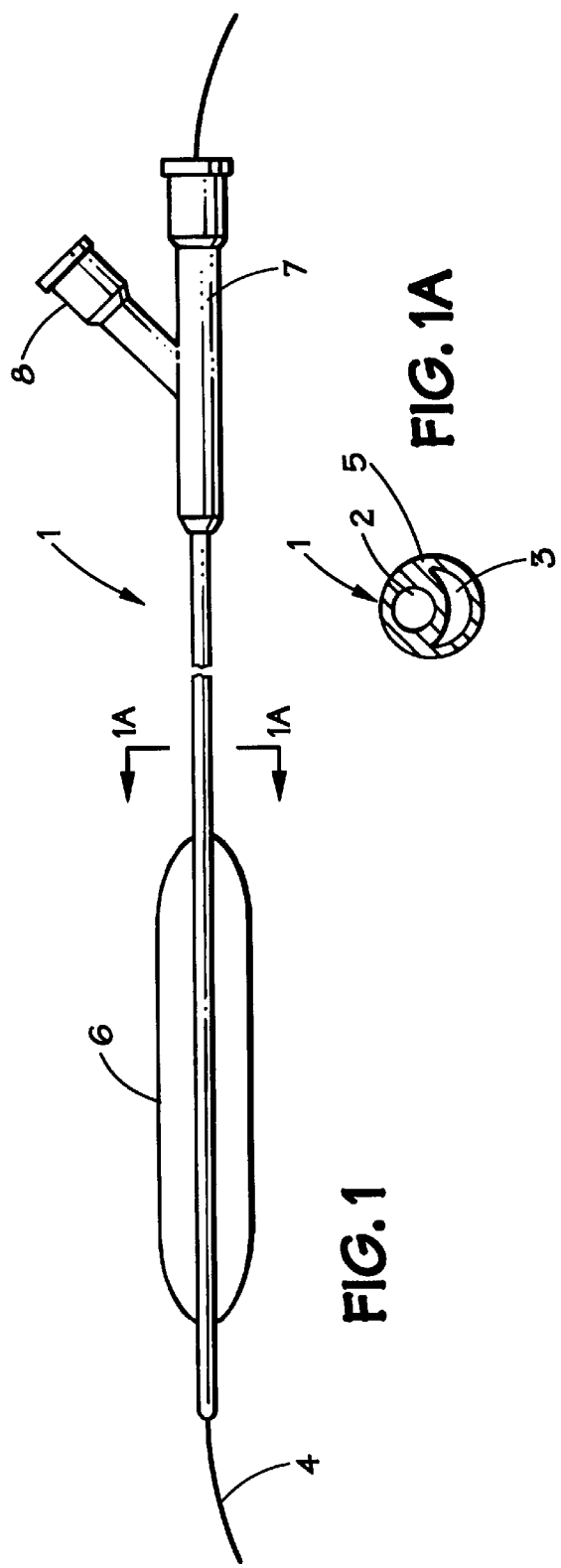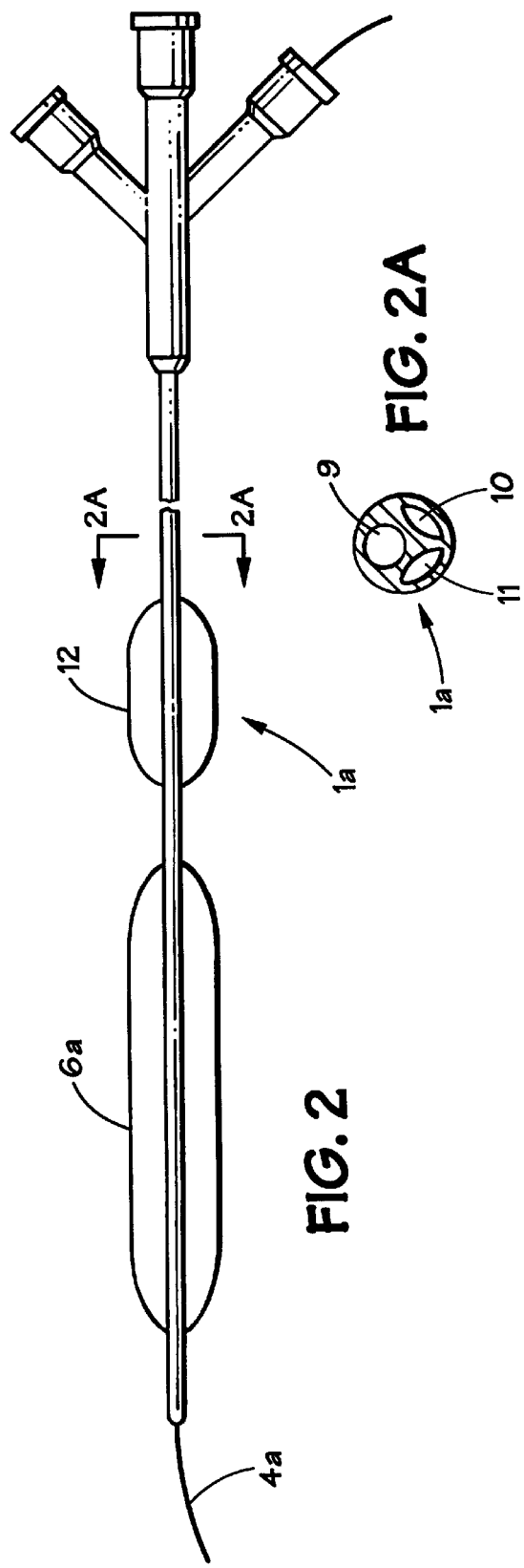

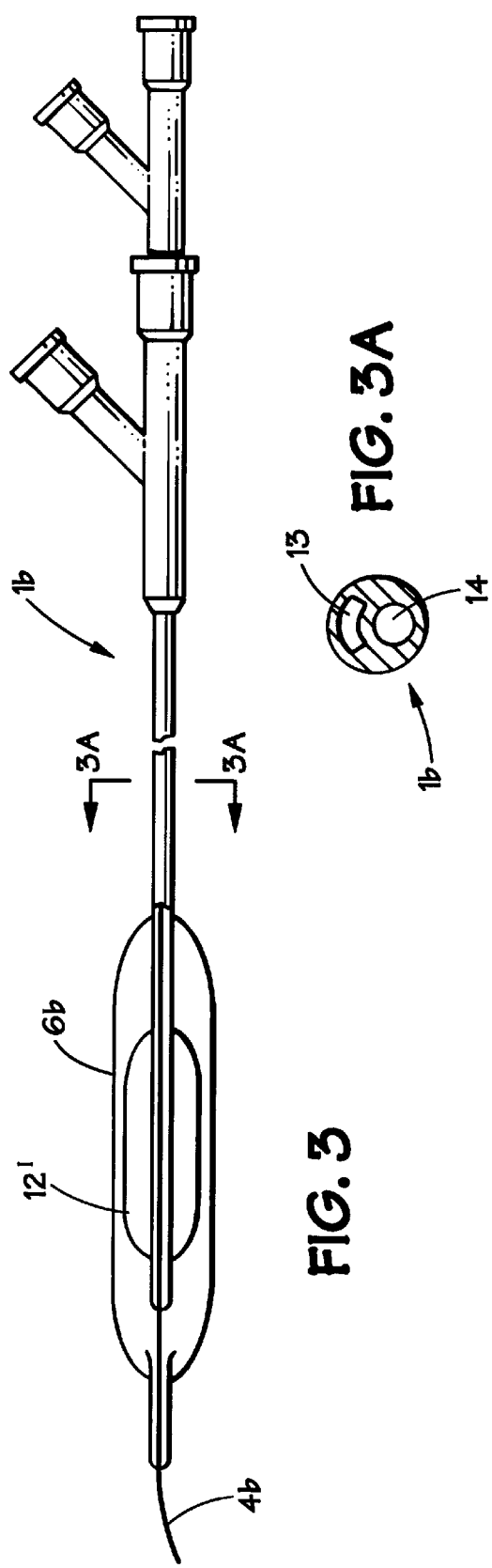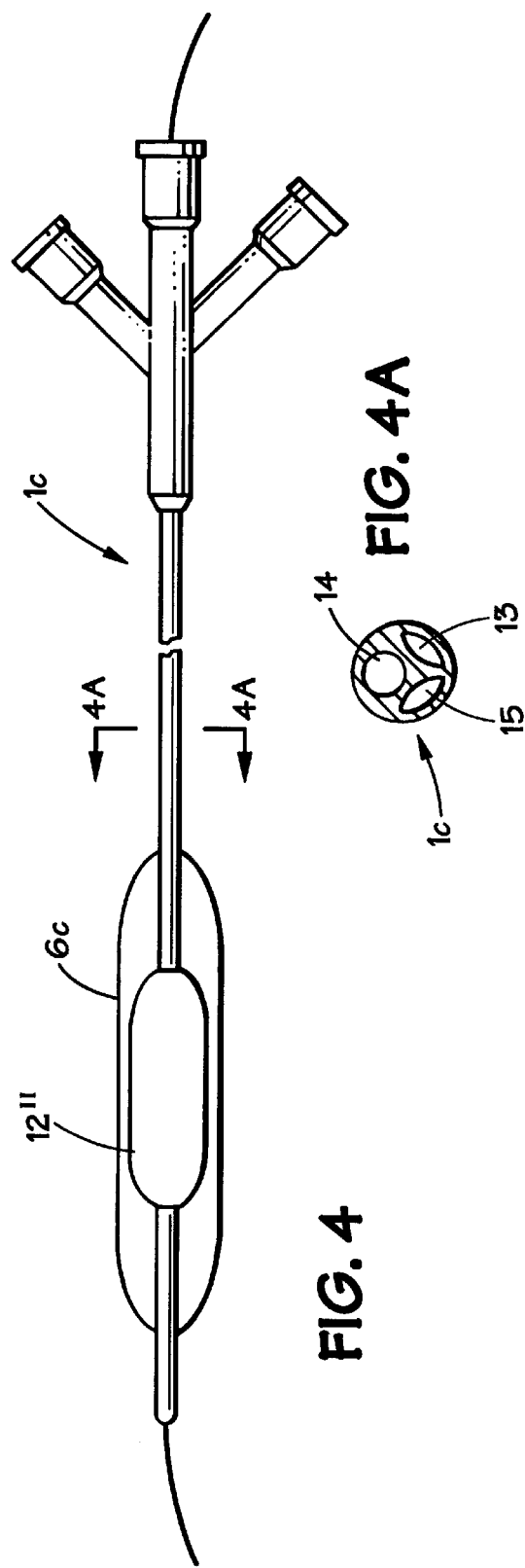

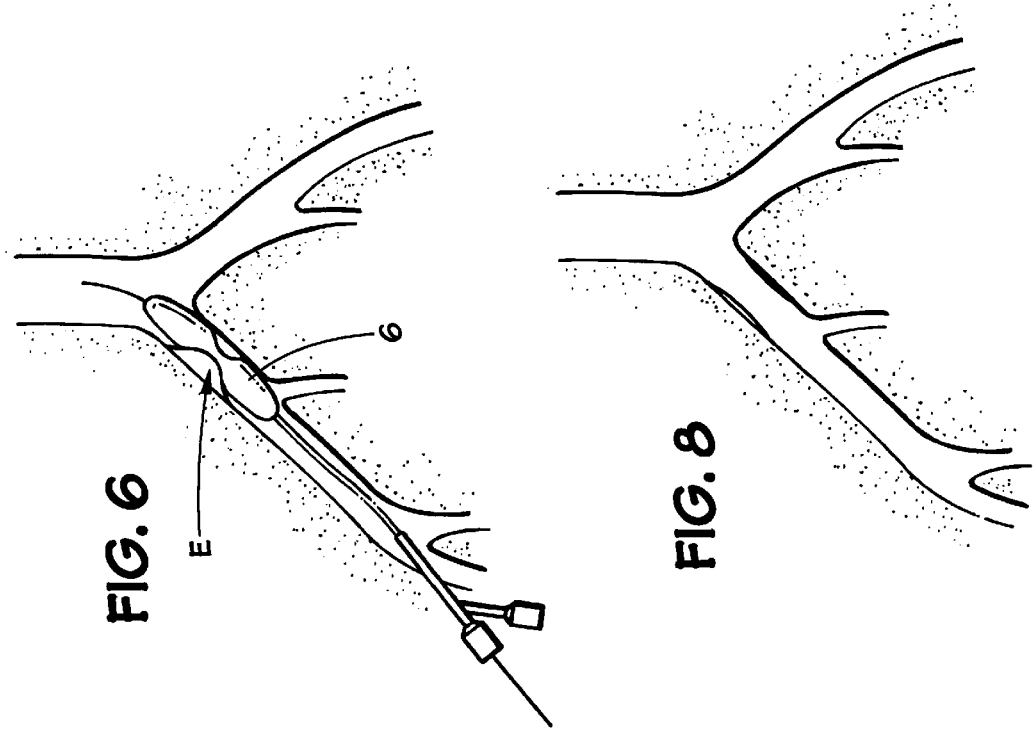
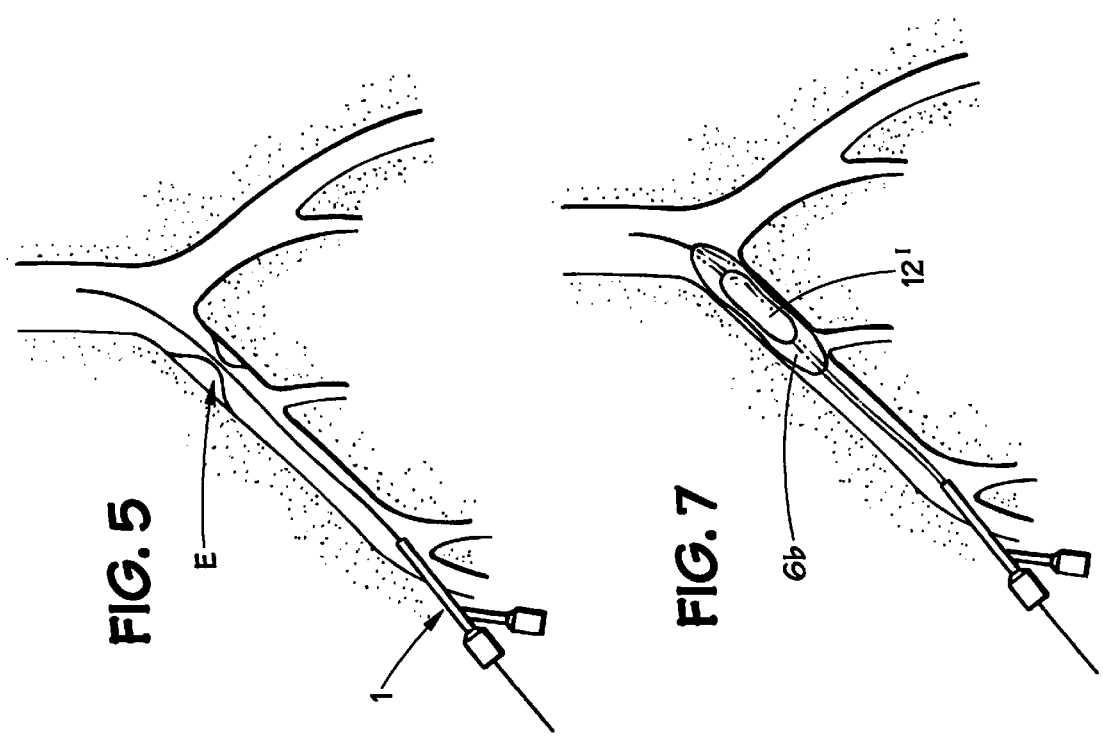

DEVICE AND METHOD TO DO ARTERIOGRAPHIES AND ANGIOPLASTIES WITH A BALLOON AND WITHOUT INJECTING A CONTRASTING MEDIA IN THE VESSEL LUMEN

FIELD OF THE INVENTION

The present invention relates to the angioplasty techniques as well as to tests on arteries having narrowed or occluded portions and more particularly to a device and a method to do arteriographies and angioplasties avoiding the injection of a contrasting medium in the vessel lumen.

DESCRIPTION OF THE PRIOR ART

The use of techniques availing of a catheter that includes a balloon to repair artery stenoses are known in the prior art. Stenosis and artery blockage decrease the nourishing flow that reaches the tissues irrigated by the affected artery. Tissue disorder caused by a decrease in irrigation may vary from necrosis of tissue to functional disorders caused by the decrease in the flow. Sometimes, secondary arteries balance the blockage of the main artery. Whenever the narrowing of the artery is treated due to the consequences of flow decrease, it should be decided whether to resort to surgery or to the dilation of the artery by making use of a balloon.

SUMMARY OF THE INVENTION

Therefore, it is an object of the present invention to provide a new device and a method to do arteriographies, allowing for the simultaneous angioplasties as by inserting a catheter and a balloon capable of copying the narrowed portion of the artery under study and providing for the contrast required to view the artery, by utilizing a contrasting medium which is circumscribed within the balloon and which is not in relationship with the patient's tissue. Therefore, it is an object of the present invention to provide a device to do arteriographies and angioplasties of the type that uses a catheter wherein at least two passages are formed, first and second passage, the first passage being utilized to run a guide wire, and which includes at least a first inflatable, elastomeric and soft balloon that is in relationship with the second passage. The latter configurates a duct whereby an arteriographic contrasting medium is introduced.

It is a further object of the present invention to provide a method to do arteriographies and angioplasties, which method employs the device described above and comprises the following steps: an artery is punctured remote of the stenoses or occlusion, an introducer is inserted thus allowing for the passage of a catheter, at least one of the balloons is moved until the narrowed portion of the artery is crossed over, the balloon is placed all along the artery under study, the balloon is filled with an arteriographic contrast substance at a very low pressure without deforming the narrowing, the balloon is kept inflated, angiography tests are done and finally the balloon is deflated.

BRIEF DESCRIPTION OF THE DRAWINGS

For further clarification and a better understanding of the object of the present invention, numerous figures have been drawn depicting some of the preferred embodiments of the present invention for purposes of illustration only, where:

FIG. 1 is a side view including a detail of the cross sectional view of a catheter in accordance with the device of the present invention;

FIG. 2 is a view similar to FIG. 1 of another embodiment of the device of the present invention;

FIG. 3 is a view similar to FIG. 1 of another embodiment of the device of the present invention;

FIG. 4 is a view similar to FIG. 1 of another embodiment of the device of the present invention;

FIGS. 5 to 8 show the stages of a preferred embodiment of the present invention.

DESCRIPTION OF THE PREFERRED EMBODIMENTS

As shown in FIG. 1, a catheter 1 is provided, the cross sectional view of which in detail shows a first passage 2 that allows a guide wire 4 to run along the shaft 5 of the catheter, also providing a second passage 3 whereby the first elastomeric, thin walled and resistent, low profile diagnosis balloon 6 is inflated. The material used for the said balloon may be latex, silicone, polyurethane or any other appropriate and elastomeric material whatsoever. The guide wire 4 as well as the balloon 6 may be operated via operation means 7 and 8. Pursuant to the present invention, the balloon 6 is carried up to the narrowed portion of the artery, as detailed when referring to FIGS. 5 to 8, and filled with an appropriate contrast media, such as a radiopaque substance. The balloon has a very thin but resistent wall, which, upon inflation, takes exactly the same form of the artery inner surface (luminogram) without deforming same. The balloon 6 shall have the length required to view the desired portion of the artery. Amongst the main features, the balloon may be inflated at a very low pressure thus not altering, as stated above, the contour of the artery under study. This device allows a guide wire to run along the artery lumen. Owing to the fact that the balloon has a very low profile, same allows for the introduction thereof in the narrowed or occluded portion of the artery, which portion is crossed over by the guide wire.

Once the luminogram is obtained by injecting the contrasting medium in the balloon, dilation of the narrowing may then proceed by using a second expanding balloon located upon the catheter that carries the diagnosis balloon, as shown in the three embodiments of the present invention illustrated in FIGS. 2, 3 and 4.

The catheter 1a in FIG. 2 has a first passage 9 for the guide wire 4a to run, a second passage 10 that allows inflation of the diagnosis balloon 6a, similar to balloon 6 in FIG. 1 and a third passage 11 permitting the expansion of the angioplasty balloon 12, located behind the diagnosis balloon 6a.

Catheter 1b in FIG. 3 includes a first passage 13 for the guide wire 4b to run and a second passage 14 which allows the diagnosis balloon 6b to be inflated, which balloon is similar to balloons 6 and 6a; said catheter also includes a container that shelters a therapeutic or angioplasty balloon 12'. The diagnosis balloon 6b carries the therapeutic balloon 12' within its lumen. The therapeutic balloon 12 runs on the wire 4b and provides consistency to the diagnosis balloon 6b.

Catheter 1c illustrated in FIG. 4 is similar to the one depicted in FIG. 3, but the therapeutic balloon 12" is fixed within the diagnosis balloon 6c anchored to the shaft of the catheter 1c, thus a third passage 15 is provided for such purpose.

The second balloons 12, 12' and 12" of the different embodiments of the present invention differ from diagnosis balloons 6 to 6c in that the former are not elastomeric for the purpose of achieving a great radial force allowing for the dilation of the narrowed artery. The angioplasty balloon shall have a low profile and shall be inflated through an independent passage of the catheter, as illustrated in the case of the three passages of the pertinent embodiments.

In the event the angioplasty balloon is sheltered inside the diagnosis balloon, the latter shall enclose a tiny catheter which houses in turn, a guide wire and said catheter shall act as a rail on which the second balloon is run, and which shall be suitably located to proceed to the dilation of the artery narrowing. The second balloon may be fixedly anchored and shall move jointly with the elastomeric balloon so as to be placed in the right location to dilate the narrowed portion of the artery.

As regards another aspect of the present invention, a method is illustrated in FIGS. 5 to 8, which method comprises the following steps: the artery is punctured and a guide wire is introduced which crosses over narrowing or occlusion "E", as illustrated in FIG. 5. This step is similar to any other angiographic procedure which may include angioplasty or not. Subsequently, an introducer means of a suitable size is placed to allow the introduction of a diagnosis-therapeutic catheter.

The device is moved forward until the narrowing "E" is crossed over, placing the diagnosis balloon of the present invention all along the artery under study, as illustrated in FIG. 6. The diagnosis balloon is filled with a contrasting substance at a very low pressure and the balloon is kept dilated. The angiographic tests are accurately done and the catheter is placed in the right angle and location so as to achieve a better view of the narrowed portion of the artery.

Once the diagnosis is made, the elastomeric balloon is deflated and the angioplasty balloon 12 is placed at the narrowing "E" level. Then, same is inflated for the purpose of dilating the injured portion of the artery. The angioplasty balloon is deflated and the diagnosis elastomeric balloon is affixed in the right position, repeating the diagnosis steps for the purpose of confirming the effectiveness of the artery dilation attained. Should dilation be suitable, the proceeding shall be deemed to be finished; should dilation fail to be suitable, the proceeding shall be repeated. If the correct results are not obtained, a balloon having a different diameter may be affixed avoiding the initial system; a "stent" may alternatively be attached. For the purpose of anchoring same, the very same non elastomeric balloon that comprises the device may be used or else, another balloon with different features may be employed.

According to the method and the device of the present invention, many advantages are gained, for instance: no contrasting medium needs to be injected in the lumen of the vessel, thus avoiding pain, possible allergy development and renal damage caused by the contrasting medium. Carbon dioxide may be alternatively used to inflate the balloon, thus obtaining the digital image by contrast reduction and not by contrast increase, as in the case of radiopaque substances. The advantage of having carbon dioxide inside and not outside the balloon lies in that a permanent image of the artery lumen is obtained, and several incidences may also be achieved with no need for further gas inoculations. Whether by changing the location of the whole device or of the non elastomeric balloon, the angioplasty may be done without changing the device and an x-ray check-up may be done simultaneously as by inflating the elastomeric balloon again in order to confirm the effectiveness of the dilation as regards reduction of artery narrowing. This procedure proves to be cost efficient since the amount of contrasting substance injected as well as the time consumed are reduced.

As the contrast media is not injected directly into the artery, substances utilized do not need to be non-ionic. Both quality and volume of contrast media can be a source of decreasing costs in addition to the advantages enumerated in relation to decreasing risks for the patient.

Having thoroughly described and established the nature of the present invention as well as the way same is to be implemented, what is claimed is:

1. A method for doing arteriographies in a portion of an artery having an inner surface, comprising the steps of:
   providing an expandable, elastomeric diagnosis balloon upon a catheter, the diagnosis balloon having an outer surface;
   introducing the diagnosis balloon into the portion of the artery to be arteriographed;
   filling the diagnosis balloon with a contrast medium to inflate the diagnosis balloon until the outer surface of the diagnosis balloon conforms to the inner surface of the portion of the artery to be arteriographed, without deforming the inner surface of the portion of the artery to be arteriographed; and
   imaging the inflated diagnosis balloon and the portion of the artery to the arteriographed.

2. The method of claim 1, including the steps of deflating the diagnosis balloon and removing the diagnosis balloon from the artery.

3. The method of claim 1, including the step of inflating the diagnosis balloon at a low pressure.

4. The method of claim 1, including the step of utilizing a radiopaque substance as the contrast medium.

5. The method of claim 1, including the step of utilizing a radiolucent substance as the contrast medium.

6. The method of claim 5, wherein the contrast medium is carbon dioxide.

7. The method of claim 1, including the steps of:
   providing an angioplasty balloon upon the catheter; and
   after the diagnosis balloon and the portion of the artery to be arteriographed are imaged, inflating the angioplasty balloon to dilate the portion of the artery which was imaged.

8. The method of claim 7, including the step of deflating the angioplasty balloon and removing the angioplasty balloon from the artery.

9. The method of claim 8, including the steps of:
   after the portion of the artery has been dilated, placing the diagnosis balloon within the portion of the artery which was dilated by the angioplasty balloon;
   filling the diagnosis balloon with a contrast medium to inflate the diagnosis balloon until the outer surface of the diagnosis balloon conforms to the inner surface of the portion of the artery which had been dilated; and
   imaging the diagnosis balloon and the portion of the artery which had been dilated.

10. The method of claim 7, including the step of providing the angioplasty balloon upon the catheter, by disposing the angioplasty balloon within the diagnosis balloon.

11. A method for doing angiographies in a portion of an artery having an inner surface, comprising the steps of:
    providing an expandable, elastomeric diagnosis balloon upon a catheter, the diagnosis balloon having an outer surface;
    introducing the diagnosis balloon into the portion of the artery to be angiographed;
    filling the diagnosis balloon with a contrast medium to inflate the diagnosis balloon until the outer surface of the diagnosis balloon conforms to the inner surface of the portion of the artery to be angiographed, without deforming the inner surface of the portion of the artery to be angiographed; and
    imaging the inflated diagnosis balloon and the portion of the artery to the angiographed.

12. The method of claim 11, including the steps of deflating the diagnosis balloon and removing the diagnosis balloon from the artery.

13. The method of claim 11, including the step of inflating the diagnosis balloon at a low pressure.

14. The method of claim 11, including the step of utilizing a radiopaque substance as the contrast medium.

15. The method of claim 11, including the step of utilizing a radiolucent substance as the contrast medium.

16. The method of claim 15, wherein the contrast medium is carbon dioxide.

17. The method of claim 11, including the steps of:

providing an angioplasty balloon upon the catheter; and after the diagnosis balloon and the portion of the artery to be angiographed are imaged, inflating the angioplasty balloon to dilate the portion of the artery which was imaged.

18. The method of claim 17, including the step of deflating the angioplasty balloon and removing the angioplasty balloon from the artery.

19. The method of claim 18, including the steps of:

after the portion of the artery has been dilated, placing the diagnosis balloon within the portion of the artery which was dilated by the angioplasty balloon;

filling the diagnosis balloon with a contrast medium to inflate the diagnosis balloon until the outer surface of the diagnosis balloon conforms to the inner surface of the portion of the artery which had been dilated; and imaging the diagnosis balloon and the portion of the artery which had been dilated.

20. The method of claim 17, including the step of providing the angioplasty balloon upon the catheter, by disposing the angioplasty balloon within the diagnosis balloon.

\* \* \* \* \*

UNITED STATES PATENT AND TRADEMARK OFFICE
CERTIFICATE OF CORRECTION

PATENT NO : 6,117,124
DATED : September 12, 2000
INVENTOR(S): Juan Carlos Parodi It is certified that error appears in the above-identified patent and that said Letters Patent is hereby corrected as shown below:

In Col. 4, Line 18, the second occurrence of "the" should be deleted, and the word - - be - - substituted therefor.

In Col. 4, Line 67, the second occurrence of "the" should be deleted, and the word - - be - - substituted therefor.

Signed and Sealed this

Twenty-ninth Day of May, 2001

*Attest:*

NICHOLAS P. GODICI

*Attesting Officer*     *Acting Director of the United States Patent and Trademark Office*